US012324787B1

(12) United States Patent
DeSimone, III et al.

(10) Patent No.: US 12,324,787 B1
(45) Date of Patent: *Jun. 10, 2025

(54) KITS FOR PREPARING AND DELIVERING PURIFIED CORTICOTROPIN

(71) Applicant: ANI Pharmaceuticals, Inc., Baudette, MN (US)

(72) Inventors: Edward M. DeSimone, III, Indianapolis, IN (US); Weijun Cheng, Middleton, WI (US); Zachary Holcomb, Waunakee, WI (US)

(73) Assignee: ANI Pharmaceuticals, Inc., Baudette, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/905,498

(22) Filed: Oct. 3, 2024

Related U.S. Application Data

(63) Continuation of application No. 18/496,150, filed on Oct. 27, 2023, now Pat. No. 12,133,831.

(60) Provisional application No. 63/381,451, filed on Oct. 28, 2022.

(51) Int. Cl.
| | |
|---|---|
| *A61K 38/00* | (2006.01) |
| *A61J 1/06* | (2006.01) |
| *A61J 1/14* | (2023.01) |
| *A61K 38/35* | (2006.01) |
| *A61K 47/10* | (2017.01) |
| *A61K 47/42* | (2017.01) |

(52) U.S. Cl.
CPC ............. *A61J 1/1443* (2013.01); *A61J 1/065* (2013.01); *A61K 38/35* (2013.01); *A61K 47/10* (2013.01); *A61K 47/42* (2013.01)

(58) Field of Classification Search
CPC ......... A61J 1/1443; A61J 1/065; A61K 38/35; A61K 47/10; A61K 47/42
See application file for complete search history.

(56) References Cited

U.S. PATENT DOCUMENTS

| | | | |
|---|---|---|---|
| 2,992,165 | A | 7/1961 | Thompson |
| 4,374,063 | A | 2/1983 | Consolazio |
| 6,461,334 | B1 | 10/2002 | Buch-Rasmussen |
| 10,232,018 | B2 | 3/2019 | Knight et al. |
| 10,286,041 | B2 | 5/2019 | Cartt |
| 11,752,199 | B1 | 9/2023 | Wright |
| 11,975,047 | B1 | 5/2024 | DeSimone, III |
| 12,102,662 | B1 | 10/2024 | DeSimone, III |
| 2007/0054957 | A1 | 3/2007 | Upadhyay |
| 2009/0216212 | A1 | 8/2009 | Fangrow, Jr. |
| 2014/0294923 | A1 | 10/2014 | Cartt et al. |
| 2018/0161243 | A1 | 6/2018 | Ariagno |
| 2018/0250365 | A1 | 9/2018 | Somera-Molina |
| 2019/0160150 | A1 | 5/2019 | Knight et al. |
| 2019/0216901 | A1 | 7/2019 | Cartt et al. |
| 2021/0100878 | A1 | 4/2021 | Lollo et al. |
| 2021/0322520 | A1 | 10/2021 | Wright |
| 2022/0031611 | A1 | 2/2022 | Bansal |
| 2022/0054595 | A1 | 2/2022 | Lollo et al. |
| 2022/0111012 | A1 | 4/2022 | Wright et al. |
| 2022/0133595 | A1 | 5/2022 | Miksztal |
| 2023/0165946 | A1 | 6/2023 | Rhee |

FOREIGN PATENT DOCUMENTS

| | | |
|---|---|---|
| WO | 2020/150738 A1 | 7/2020 |
| WO | 2022/131919 A1 | 6/2022 |
| WO | 2023/034819 A1 | 3/2023 |

OTHER PUBLICATIONS

Office Action dated Oct. 16, 2024 issued in U.S. Appl. No. 18/818,974. (24 pages).
Mallinckrodt (ACTHAR—repository corticotropin injection, Injection Instructions; ARDUS/01-13/0417/0033, 2017.
Mallinckrodt Label—NIH/DailyMed. Drug Archives, 2016 label.
Citron Reports Further Results from Laboratory Testing: Questcor is Deceiving the FDA and Investors, H.P. Acthar Gel's Specified Active Ingredient Less Than 20% of the Label Specification, Bioactivity of Deamidated Hormone Fragment Far Lower than Pure ACTH, The FDA has been Notified, Mar. 14, 2014, 10 pgs.
Acthar Gel (repository corticotropin injection), Package Insert, Mallinckrodt ARD LLC, 2021, 22 pgs.
Repository Corticotropin (H.P. Acthar Gel), BlueCross BlueShield of North Carolina, 2012, 5 pgs.
Purified Cortrophin(R) Gel Repository Corticotropin Injection U.S. P., Organon Inc., (1972), 3 pgs.
USP, Notice of Intent to Revise:<660> Container Glass, (Year:2023) (2 pages).
Office Action issued in U.S. Appl. No. 18/495,932 dated Jan. 11, 2024 (27 pages).
Office Action issued in U.S. Appl. No. 18/496,170 dated Sep. 25, 2024 (13 pages).
Wallace I, Cunningham S, Lindsay J. The diagnosis and investigation of adrenal insufficiency in adults. Ann Clin Biochem. Sep. 2009;46(Pt 5):351-67. (Year: 2009) 17 pgs.
Office Action dated Mar. 13, 2024 issued in corresponding U.S. Appl. No. 18/496,150 (9 pages)
Mallinckrodt, Acthar: Step-by-Step Self-Injection Instructions (repository corticotropin injection), 2017 (28 pages).
Mallinckrodt Label—NIH/DailyMed. Drug Archives, 2016 label (18 pages).

(Continued)

*Primary Examiner* — Jeanette M Lieb
(74) *Attorney, Agent, or Firm* — Rothwell, Figg, Ernst & Manbeck, P.C.

(57) ABSTRACT

A kit and sterile preparation of purified corticotropin and methods relating thereto in which the preparation includes corticotropin extracted from a whole porcine pituitary gland including both anterior and posterior portions, and having proteins or peptides having a molecular weight higher than 4.6 kDa removed. Methods of manufacturing, testing, increasing stability, storage, and use of the purified corticotropin are also provided.

20 Claims, 2 Drawing Sheets

Specification includes a Sequence Listing.

(56) References Cited

OTHER PUBLICATIONS

Acthar Gel, repository corticotropin injection. Package Insert. Mallinckrodt ARD. U.S. Food and Drug Administration website. https://www.accessdata.fda.gov/drugsatfda_docs/label/2021/008372s068lbl.pdf (Revised Feb. 2021). 21 pages.

Riniker et al. Revised amino-acid sequences for porcine and human adrenocorticotrophic hormone. Nat New Biol. Jan. 26, 1972;235(56):114-5.

(step a)

(step b)

(step c)

(step d)

KITS FOR PREPARING AND DELIVERING PURIFIED CORTICOTROPIN

CROSS-REFERENCE TO RELATED APPLICATIONS

This application is a continuation of U.S. application Ser. No. 18/496,150, filed Oct. 27, 2023, which claims priority benefit of U.S. provisional application No. 63/381,451, filed Oct. 28, 2022, the disclosures of which are incorporated herein by reference in its entirety.

INCORPORATION-BY-REFERENCE OF SEQUENCE LISTING

The instant application contains a Sequence Listing which has been submitted via EFS-Web and is hereby incorporated by reference in its entirety. Said Sequence Listing, created on Oct. 25, 2023, is named "5484-101US3.xml" and is 4,096 bytes in size.

FIELD OF THE DISCLOSURE

This disclosure relates to kits, pharmaceutical compositions and methods including making, using, and formulating purified corticotropin.

BACKGROUND

Corticotropin is a polypeptide referred to as adrenocorticotropic hormone (ACTH). Corticotropin has been derived from anterior portions of porcine pituitary glands as an extract.

In such products, monitoring and control of viruses originating from animal-derived products has been a key safety concern. Accordingly, there is a need for improved manufacturing processes to detect and remove or inactivate viruses.

While pharmaceutical compositions of ACTH have been prepared in a sterile solution of gelatin, the high concentration of gelatin makes use of HPLC challenging due to the interference of the gelatin components. Accordingly, there is a need for improved corticotropin formulations, products, and processes.

SUMMARY OF THE INVENTION

In one aspect, the present disclosure includes a method of manufacturing a sterile preparation of purified corticotropin, including extracting corticotropin from a whole porcine pituitary gland including both anterior and posterior portions, and removing proteins or peptides having a molecular weight higher than ACTH. In some aspects, the sterile preparation of purified corticotropin is preservative-free or antimicrobial-free.

In some aspects, methods of the present disclosure include performing SEC-HPLC, RP-HPLC, and stability testing of the formulation of the present disclosure.

In some aspects, the method of manufacturing further includes performing forced degradation of the sterile preparation under acidic, basic, thermal, photolytic, and/or oxidative stress conditions to produce a sample. In some aspects, the method of manufacturing further includes analyzing the sample using reversed-phase High Performance Liquid Chromatography (RP-HPLC). In some aspects, the method of manufacturing further includes subjecting the sterile preparation to sodium dodecyl sulfate-polyacrylamide gel electrophoresis (SDS-PAGE) or Western blotting and identifying impurities. In some aspects, the method of manufacturing further includes removing porcine genomic DNA and testing the sterile preparation of purified corticotropin using quantitative polymerase chain reaction (qPCR).

In some aspects, the method of manufacturing further includes performing aseptic filtration. In some aspects, the method of manufacturing does not include a terminal sterilization process.

In another aspect, the present disclosure includes a method of storing and warming a sterile corticotropin composition including storing the sterile corticotropin composition in a vial, e.g., a multiple-dose vial comprising 80 USP units/mL of the sterile corticotropin composition, wherein the vial comprises a rubber stopper coated with cross-linked silicones, at a temperature of 2° to 8° C.; and then warming the vial to a temperature of 18° to 26° C. before injection. In one aspect, the sterile corticotropin composition has physical properties such that it is a solid gel at 2° to 8° C. and is a liquid gel at 18° to 26° C. In one aspect, the warming step involves rolling the vial between two hands for at least two minutes. In one aspect, the stopper comprises a coating comprising silicone oils of different molecule weights. In one aspect, the vial is a 5 mL multiple-dose vial. In one aspect, the vial further comprises a removable cap covering the stopper. In one aspect, the vial has a diameter of 13 mm. In one aspect, the vial comprises an aluminum seal. In one aspect, the removable cap has a diameter of 13 mm. In one aspect, the vial is borosilicate USP Type I glass.

In another aspect, the present disclosure includes a vial containing a filter-sterilized preparation of purified corticotropin comprising 80 USP units per mL of corticotropin, 0.5% w/w phenol, 15.0% w/w gelatin, water for injection (WFI), wherein the gelatin is Type A, wherein the vial is not terminally sterilized. In one aspect, the gelatin is pyrogen-free. In one aspect, the vial further comprises acidified WFI having a pH of 2.8 to 3.2. In one aspect, the vial further comprises hydrochloric acid and/or sodium hydroxide. In one aspect, the filter-sterilized preparation has not more than 0.05 USP Vasopressin Units/USP Corticotropin Units. In one aspect, the vial further comprises 1 mg/ml purified corticotropin powder, 150 mg/ml type A gelatin, 5 mg/ml phenol, hydrochloric acid, sodium hydroxide, and 1 ml water for injection. In one aspect, the gelatin has a gel point in the range of 18 to 24° C. In one aspect, the gelatin has a pH of 5.9 to 6.2. In one aspect, the filter-sterilized preparation has less than 6000 particles ≥10 μm. In one aspect, the filter-sterilized preparation has less than 600 particles ≥25 μm. In one aspect, the filter-sterilized preparation is free of acetic acid. In one aspect, the filter-sterilized preparation of purified corticotropin is a prolonged release formulation.

In another aspect, the present disclosure includes a method of treating a subject having acute exacerbations of multiple sclerosis (MS) comprising administering to the subject 40-80 USP units/ml of a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A, daily for 5-25 days, wherein the purified corticotropin is a naturally derived extract from a whole porcine pituitary gland including both anterior and posterior portions.

In another aspect, the present disclosure includes a method of treating a subject having acute gouty arthritis, severe psoriasis, atopic dermatitis, or allergic conjunctivitis, comprising administering a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A to the subject, wherein the purified corticotropin is a naturally derived extract from a whole porcine pituitary gland including both anterior and posterior portions.

In another aspect, the present disclosure includes a method of treating a subject having acute gouty arthritis comprising administering a sterile preparation of purified corticotropin and a second therapeutic agent to the subject, wherein the purified corticotropin is a naturally derived extract from a whole porcine pituitary gland including both anterior and posterior portions.

In one aspect, the methods of the present disclosure include administering the sterile preparation of purified corticotropin by withdrawing the sterile preparation from a vial with a first needle having a first gauge size with a first diameter, and injecting the sterile preparation into the subject with a second needle having a second gauge size with a second diameter. In one aspect, the first gauge size is 20 G and the second gauge size is 23 G.

In one aspect, the present disclosure includes verifying adrenal responsiveness after administering the sterile preparation for a first time. In some aspects, adrenal responsiveness is verified by a rise in urinary corticosteroid values and plasma corticosteroid values. In some aspects, adrenal responsiveness is verified by administering 20 to 80 USP units/ml of the sterile preparation. In some aspects, 20 to 80 USP units/ml of the sterile preparation is administered in a single injection or over a series of two or more injections. In some aspects, the subject has a rise in urinary corticosteroid values and plasma corticosteroid values after administering the sterile preparation for a first time subcutaneously or intramuscularly. In some aspects, the sterile preparation of purified corticotropin is administered to the subject for more than one month, and the method further comprises administering corticosteroids to the subject. In some aspects, the subject is suspected to have a sensitivity to porcine protein, and the method further comprises performing skin testing prior to administering the sterile preparation and observing the subject for a reaction after administering the sterile preparation. In some aspects, the subject is suspected to have an infection, and the method further comprises administering an appropriate anti-infective therapy. In some aspects, the subject is pregnant with a child while administering the sterile preparation of purified corticotropin and the method further comprising observing the child for signs of hypoadrenalism. In some aspects, the sterile preparation of purified corticotropin is stored in the vial at 2° C. to 8° C., wherein the sterile preparation is a solid gel when stored, and warming the sterile preparation of purified corticotropin to a liquid gel before administering the sterile preparation. In some aspects, the sterile preparation is warmed by rolling the vial between two hands for at least 2 minutes. In some aspects, the vial comprise a top end with a cap and a rubber or silicone stopper, and the method further comprising removing the cap from the vial and wiping the stopper with a sterile alcohol wipe.

In another aspect, the present disclosure includes a method of administering a sterile corticotropin composition to a human subject, comprising: warming a vial containing the sterile corticotropin composition from a temperature of 2° to 8° C. to a temperature of 18° to 26° C.; withdrawing the sterile corticotropin composition from the vial with a first needle having a first gauge size with a first diameter; replacing the first needle with a second needle having a second gauge size with a second diameter that is different from the first diameter; and injecting the sterile preparation into the subject thereof with the second needle. In one aspect, the warming is performed in a range of 30 seconds to 3.5 minutes, 1 minute to 2.5 or 3 minutes, 1.5 to 2 minutes or any amount of time within the range of 30 seconds to 3.5 minutes. In one aspect, the warming is by rolling the vial between two hands. In one aspect, the injecting is subcutaneously or intramuscularly. In one aspect, the method includes injecting 80 (United States Pharmacopeia) USP units of the sterile corticotropin composition to the patient, or injecting less than 80 USP, or injecting at least two injections of less than 80 USP units. In one aspect, the method includes observing the site of injection after step d) for skin reactions. In one aspect, the method includes verifying a rise in urinary corticosteroid values and plasma corticosteroid values after injecting 20 to 80 USP units/ml of the sterile corticotropin composition. In one aspect, the method also includes administering a rapidly acting corticosteroid to the subject. In one aspect, the method includes administering an anti-infective drug. In one aspect, the method includes, when the subject is pregnant with a child during the administering, observing the child for signs of hypoadrenalism before or after birth.

In another aspect, the present disclosure includes a method of using a sterile preparation of purified corticotropin including administering a sterile preparation of purified corticotropin to an individual in need thereof, wherein administering the sterile preparation of purified corticotropin comprises the steps of: withdrawing the sterile preparation from a vial with a first needle having a first gauge size with a first diameter, and injecting the sterile preparation into the individual with a second needle having a second gauge size with a second diameter.

In another aspect, the present disclosure includes a method of selecting a patient for treatment with a purified corticotropin injection comprising: a) measuring a first plasma corticosteroid level of the patient; b) administering a single injection of the purified corticotropin to the patient; c) measuring a second plasma corticosteroid level of the patient after the administering; and d) selecting the patient for treatment if the second plasma corticosteroid level is higher than the first plasma corticosteroid level. In one aspect, the method further involves measuring a first urine corticosteroid level of the patient before step b) and measuring a second urine corticosteroid level of the patient after step b); and selecting the patient for treatment if the second urine corticosteroid level is higher than the first urine corticosteroid level.

In another aspect, the present disclosure includes a kit comprising a vial containing a sterile preparation of purified corticotropin, a first needle having a first gauge size with a first diameter, and a second needle having a second gauge size with a second diameter, wherein the sterile preparation comprises 80 USP units per mL of corticotropin, phenol, type A gelatin, water for injection (WFI), hydrochloric acid, and sodium hydroxide, wherein the vial is not terminally sterilized. In one aspect, the vial is a 5 mL multiple-dose vial. In one aspect, the first diameter is wider than the second diameter, e.g., the first gauge size is 20 G and the second gauge size is 23 G.

According to any of the aspects described herein, the present disclosure includes any one or more of the following aspects: the purified corticotropin comprises amino acids 1-39 of SEQ ID NO: 1; the purified corticotropin comprises an extract from whole porcine pituitary gland including both anterior and posterior portions of the whole porcine pituitary gland; the phenol is multi-compendial grade phenol; the vial is a multiple-dose vial comprising a stopper, e.g., a rubber stopper coated with cross-linked silicones; the stopper comprises a coating comprising silicone oils of different molecule weights; the multiple-dose vial is a 5 mL multiple-dose vial; the multiple-dose vial further comprises a removable cap covering the stopper; the multiple-dose vial has a diameter of 13 mm; the multiple-dose vial comprises an aluminum seal; the removable cap has a diameter of 13 mm; the multiple-dose vial is borosilicate USP Type I glass; the filter-sterilized preparation has not more than 0.05 USP Vasopressin Units/USP Corticotropin Units;

In some aspects, the purified corticotropin includes a) a polypeptide consisting of amino acids 1-39 of SEQ ID NO: 1.

In some aspects, the formulations contain 80 U/ml purified corticotropin powder, 150 mg/ml type A gelatin, 5 mg/ml phenol, hydrochloric acid, sodium hydroxide, and 1 ml water for injection. In some aspects, the gelatin has a pH of 5.9 to 6.2. In some aspects, the filter-sterilized preparation has less than 6000 particles ≥10 μm. In some aspects, the filter-sterilized preparation has less than 600 particles ≥25 μm. In some aspects, the filter-sterilized preparation is free of acetic acid. In some aspects, the filter-sterilized preparation of purified corticotropin is a prolonged release formulation.

According to any of the aspects described herein, the present disclosure further includes a purified corticotropin that is free of at least one of the following viruses: Bovine viral diarrhea virus (BVDV); Encephalomyocarditis virus (EMCV); Foot and mouth disease virus (FMDV); Hepatitis E virus (HEV); Nipah Virus; Porcine adenovirus (PAV); Porcine astrovirus (PAstV); Porcine circovirus (PCV); Porcine cytomegalovirus (PCMV); Porcine endogenous retrovirus (PERV); Porcine enterovirus (PEV); Porcine hemagglutinating encephalomyelitis virus (PHE-CoV); Porcine hokovirus (PHoV); Porcine influenza virus; Porcine lymphotropic herpesvirus; Porcine parvovirus (PPV); Porcine Reproductive and Respiratory Syndrome virus (PPRSV); Porcine teschovirus (PTV); Pseudorabies virus (PRV); Rabies virus; Reovirus; Rotavirus; Sapovirus; Seneca valley virus (SVV); Swine vesicular disease virus (SVDV); Transmissible gastroenteritis virus (TGEV); Vesicular stomatitis virus (VSV). According to any of the aspects described herein, the present disclosure further includes a purified corticotropin that is free of at least one of the following zoonotic pathogens: (i) *Ascaris* species, *cryptosporidium* species, *Echinococcus*, Strongyloids sterocolis, and *Toxoplasma gondii* in fecal matter; (ii) *Leptospira* species, *Mycoplasma* hyopneumoniae, porcine reproductive and respiratory syndrome virus (PRRSV), pseudorabies, transmissible gastroenteritis virus (TGE)/Porcine Respiratory Coronavirus, and *Toxoplasma Gondii* by determining antibody titers; (iii) Porcine Influenza; (iv) the following bacterial pathogens as determined by bacterial culture: *Bordetella* bronchiseptica, Coagulase-positive staphylococci, Coagulase-negative staphylococci, Livestock-associated methicillin resistant *Staphylococcus aureus* (LA MRSA), *Microphyton* and *Trichophyton* spp.; (v) Porcine cytomegalovirus; and (vi) *Brucella suis*.

Other features and characteristics of the subject matter of this disclosure, as well as the methods of operation, functions of related elements of structure and the combination of parts, and economies of manufacture, will become more apparent upon consideration of the following description and the appended claims, all of which form a part of this specification.

DETAILED DESCRIPTION

Figure 1:
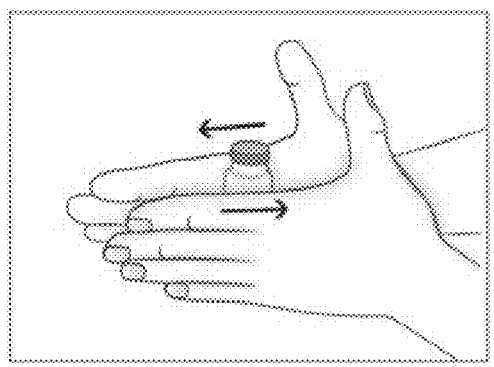
FIG. 1 shows steps of a method of using a vial containing a sterile preparation of purified corticotropin according to the present disclosure.
Figure 1:
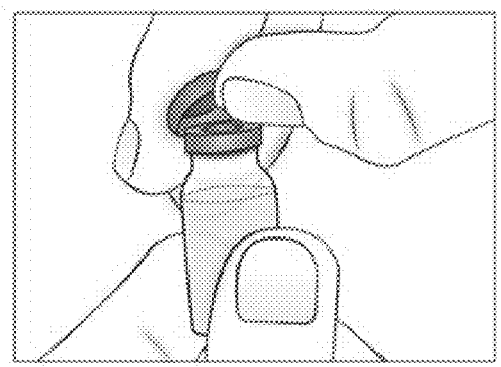
Figure 1:
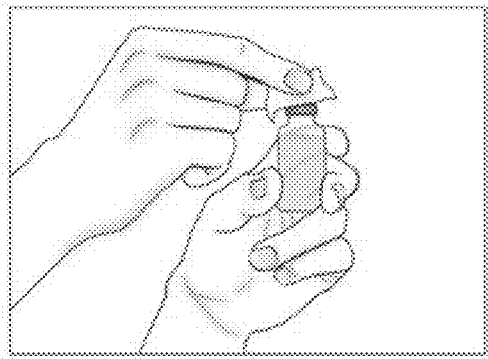
Figure 1:
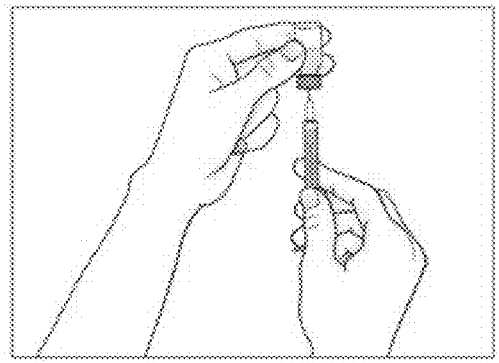
Figure 2:
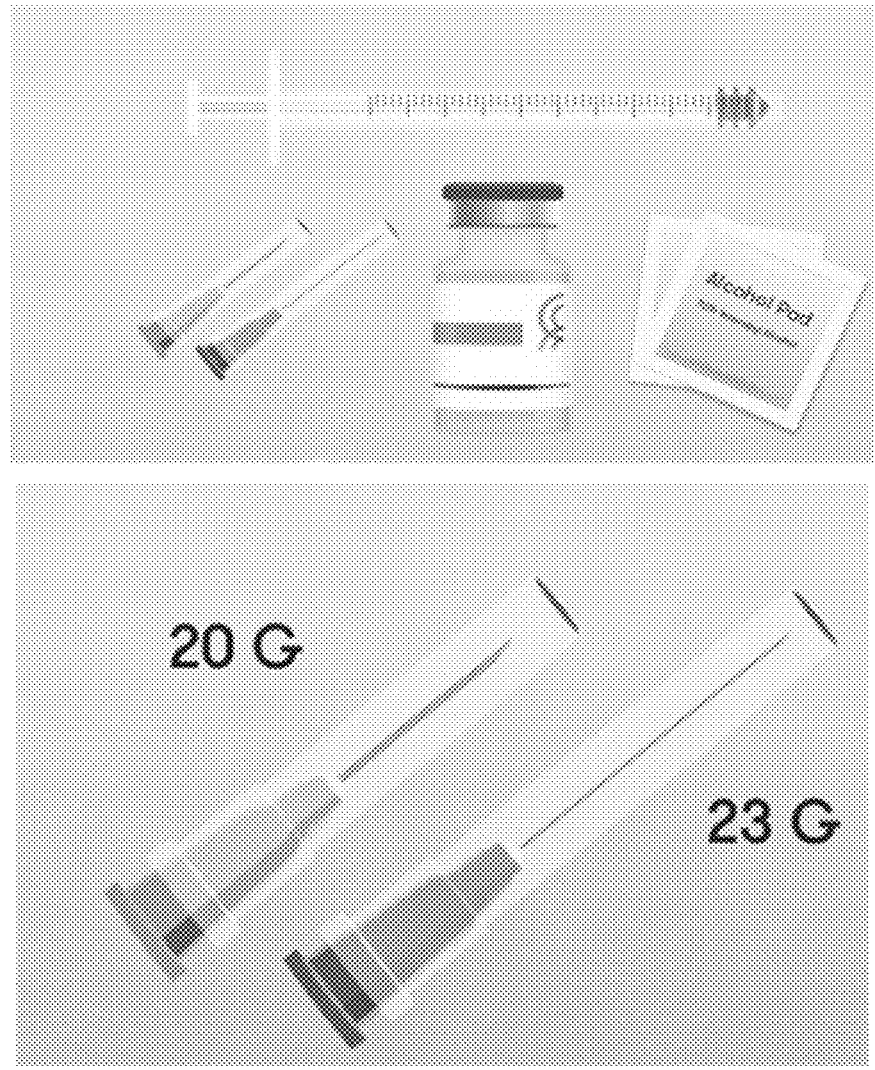
FIG. 2 shows components including a vial, a syringe, two needles of different gauges, and alcohol pads.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or embodiments so described.

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus may be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" may be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation may apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of," as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about +10% of the numerical value. In another aspect, the degree of flexibility can be within about +5% of the numerical value. In a further aspect, the degree of flexibility can be within about +2%, +1%, or +0.05%, of the numerical value. Numerical quantities given are approximate, meaning that the term "around," "about" or "approximately" can be inferred if not expressly stated.

As used herein, the term "pharmaceutically acceptable" refers to solvents, co-solvents, surfactants, carriers, diluents, excipients, buffers, salts, and/or other components that are compatible with the other ingredients of the formulation and are not deleterious to the recipient thereof.

Generally herein, the term "or" includes "and/or."

As used herein, a plurality of compounds, elements, or steps may be presented in a common list for convenience. However, these lists may be construed as though each member of the list is individually identified as a separate and unique member. Thus, no individual member of such list may be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a formulation or method of treating a certain subject is intended to and does find direct support for embodiments related to compositions, formulations, and methods described in any other part of this disclosure, even if those method steps, active agents, kits, or compositions are not re-listed in the context or section of that embodiment or aspect.

According to the present disclosure, a purified corticotropin composition includes a 39-amino acid peptide, also known as adrenocorticotropic hormone or ACTH or ACTH (1-39). The purified corticotropin of the present disclosure is obtained from whole porcine pituitary glands. The formulation stimulates the functioning adrenal cortex to produce and secrete adrenocortical hormones. The naturally derived extract is purified and formulated in gelatin and has a prolonged release profile. Purified cortrophin gel is a sterile preparation of the complex mixture that may comprise 80 USP units per mL of purified corticotropin, phenol, gelatin, and water for injection. In some aspects, the pH is adjusted with hydrochloric acid and sodium hydroxide. In some aspects, the purified corticotropin of the present disclosure is preservative-free or antimicrobial-free. Purified Cortrophin Gel comprises the porcine derived ACTH (1-39) with the following amino acid sequence SYSMEHFRW-GKPVGKKRRPVKVYPNGAEDELAEAFPLEF (SEQ ID NO: 1). In certain aspects, a composition according to the present disclosure is not a vaccine. In certain aspects, a composition according to the present disclosure is not in the form of nanoparticles. In certain aspects, a composition according to the present disclosure is not a combination of corticotropin with one or more non-corticotropin active agents.

Uses and Treatments

Purified cortrophin gel may be used for and to treat a number of disorders for which steroids are also indicated. In some aspects, the present disclosure includes using purified cortrophin gel to treat the following disorders: ulcerative colitis, rheumatic disorders, including as an adjunctive therapy for short-term administration (to tide the patient over an acute episode or exacerbation) in psoriatic arthritis, rheumatoid arthritis (including juvenile rheumatoid arthritis (selected cases may require low-dose maintenance therapy)), ankylosing spondylitis, and acute gouty arthritis; collagen diseases, including during an exacerbation or as maintenance therapy in selected cases of systemic lupus erythematosus, and systemic dermatomyositis (polymyositis); dermatologic diseases, including severe erythema multiforme (stevens-johnson syndrome) and severe psoriasis; allergic states, including atopic dermatitis and serum sickness; ophthalmic diseases, including severe, acute, and chronic allergic and inflammatory processes involving the eye and its adnexa (e.g., allergic conjunctivitis, keratitis, iritis and iridocyclitis, diffuse posterior uveitis and choroiditis, optic neuritis, chorioretinitis, and anterior segment inflammation); respiratory diseases, including symptomatic sarcoidosis; edematous states, including to induce a diuresis or a remission of proteinuria in the nephrotic syndrome without uremia of the idiopathic type or that due to lupus erythematosus; and nervous system, including acute exacerbations of multiple sclerosis.

Ulcerative colitis (UC) is a multifactorial, immune-mediated, chronic inflammatory condition of the colonic mucosa affecting children and adults, with peak incidence in young adulthood. UC is a type of inflammatory bowel disease (IBD) that is characterized by recurring episodes of inflammation frequently manifesting as diarrhea with or without blood, urgency, tenesmus, and incontinence. Patients with involvement isolated to the distal colon may present with constipation accompanied by discharge of blood and mucous. The severity of disease ranges from mild to severe, defined by frequency of bowel movements, presence or absence of blood, and other systemic symptoms (e.g., fever, fatigue, weight loss, anemia). Disease severity and response to therapy are assessed by monitoring clinical symptoms, endoscopy, imaging, and laboratory values. Approximately 15% of patients experience a severe course, with 20% of this population requiring hospitalization. Complications of acute severe UC include severe blood loss including hemorrhage, fulminant colitis and toxic megacolon, and perforation. Chronic disease can result in strictures, dysplasia, and colorectal cancer. Patients with UC have a slightly higher mortality compared to the general population and it is highest in the first year after diagnosis. Medical management and early colectomy for treatment non-responders have contributed to a sharp decline in morality. Additionally, up to twenty-five percent of patients have extra-intestinal manifestations of UC, which can include numerous organ systems and can contribute to significant extra-intestinal morbidity.

In some aspects, the method includes treating a subject having primary adrenal insufficiency or Addison disease with 40 to 80 units of the formulation of the present disclosure in a single dose. In some aspects, the method includes treating a subject having psoriatic arthritis with 80 units of the formulation of the present disclosure twice per week for up to 6 months. In some aspects, the method includes treating a subject having rheumatoid arthritis with 80 units of the formulation of the present disclosure twice per week for up to 6 months. In some aspects, the method includes treating a subject having rheumatoid arthritis or psoriatic arthritis additionally with one or more of a steroid, methotrexate, Leflunomide, Hydroxychloroquine, azathioprine, mycophenolate, Cyclosporine, Apremilast, Sulfasalazine, etanercept, adalimumab, infliximab, certolizumab pegol, golimumab, Ustekinumab, Secukinumab, ixckizumab, anakinra, abatacept, tofacitinib, brodalumab, retinoids, guselkumab, tildrakizumab, and rizankizumab.

In some aspects, the method includes treating a subject having ankylosing spondylitis with 80 units of the formulation of the present disclosure twice per week for 6 to 12 months. In some aspects, the method includes treating a subject having ankylosing spondylitis additionally with one or more of etanercept, adalimumab, infliximab, certolizumab pegol, golimumab, naproxen, celecoxib, ibuprofen, Secukinumab, rituximab, ustekinumab, secukinumab, methotrexate, and sulfasalazine.

In some aspects, the method includes treating a subject having acute gouty arthritis with 25 to 40 units of the formulation of the present disclosure. In some aspects, the method includes treating a subject having acute gouty arthritis with 100 units of the formulation of the present disclosure. In some aspects, the method includes treating a subject having acute gouty arthritis additionally with one or more of a NSAID, a steroid, Colchicine, Canakinumab, anakinra, xanthine oxidase inhibitors, allopurinol, febuxostat, uricosurics, probenecid, lesinurad and pegloticase.

In some aspects, the method includes treating a subject having systemic lupus erythematosus with 80 units of the formulation of the present disclosure twice per week for 6 to 12 months. In some aspects, the method includes treating a subject having systemic lupus erythematosus additionally with one or more of a steroid, methotrexate, azathioprine, mycophenolate, hydroxychloroquine, leflunomide, cyclophosphamide, belimumab, rituximab, calcineurin inhibitors (tacrolimus and sirolimus and cyclosporine), TNF inhibitors, abatacept, and tocilizumab.

In some aspects, the method includes administering 120 units comprising an injection amount of 1.5 mL.

In some aspects, the method includes administering 80 units comprising an injection amount of 1 mL.

In some aspects, the method includes administering 40 units comprising an injection amount of 0.5 mL.

In some aspects, the method includes administering 25 units comprising an injection amount of 0.3125 mL.

In some aspects, the method includes administering 20 units comprising an injection amount of 0.25 mL.

In some aspects, the method includes treating a subject having systemic dermatomyositis with 80 units of the formulation of the present disclosure twice per week for 6 to 12 months. In some aspects, the method includes treating a subject having systemic dermatomyositis with one or more of a steroid, Hydroxychloroquine, methotrexate, azathioprine, cyclosporine, tacrolimus, mycophenolate, cyclophosphamide, intravenous immunoglobulin (IVIG), rituximab, abatacept, TNF inhibitors, and tocilizumab.

In some aspects, the method includes treating a subject having Stevens-Johnson syndrome with 80 units of the formulation of the present disclosure once or twice per week for up to 12 months. In some aspects, the method includes treating a subject having Stevens-Johnson syndrome with one or more of a steroid, cyclosporine, IVIG, Iinfliximab, and etanercept.

In some aspects, the method includes treating a subject having severe psoriasis with 80 units of the formulation of the present disclosure once or twice per week for up to 6, 9, or 12 months. In some aspects, the method includes treating a subject having severe psoriasis with one or more of Apremilast, methotrexate, cyclosporine, acitretin, adalimumab, etanercept, infliximab, ustekinumab, ixekizumab, secukinumab, brodalumab, and guselkumab.

In some aspects, the method includes treating a subject having serum sickness with 20-80 units of the formulation of the present disclosure for 48 hours, optionally in combination with a steroid.

In some aspects, the method includes treating a subject having adopic dermatitis with 80 units of the formulation of the present disclosure once or twice per week for up to 6 or 12 months, optionally in combination with one or more of Methotrexate, microphenylate mofetil, azathioprine, and dupilumab.

In some aspects, the method includes treating a subject having Allergic conjunctivitis, Keratitis, Iritis, iridocyclitis, Diffuse posterior uveitis, choroiditis, Optic neuritis, Chorioretinitis, or Anterior segment inflammation with 80 units of the formulation of the present disclosure once, twice, or three times per week for up to 14 months, optionally in combination with a steroid, methotrexate, azathioprine, mycophenolate, cyclosporine, tacrolimus, Cyclophosphamide, chlorambucil, etanercept, adalimumab, infliximab, certolizumab pegol, golimumab, tocilizumab, Sarilumab, secukinumab, canakinumab, anakinra, gevokizumab, daclizumab, ustekinumab, rituximab, abatacept, filgotinib, tofacitinib, and apremilast.

In some aspects, the method includes treating a subject having optic neuritis with 5 days at 80 units and 10 days at 40 units, optionally in combination with a steroid, methotrexate, azathioprine, mycophenolate, cyclosporine, tacrolimus, Cyclophosphamide, chlorambucil, etanercept, adalimumab, infliximab, certolizumab pegol, golimumab, tocilizumab, Sarilumab, secukinumab, canakinumab, anakinra, gevokizumab, daclizumab, ustekinumab, rituximab, abatacept, filgotinib, tofacitinib, and apremilast. In some aspects, the method includes treating a subject having symptomatic sarcoidosis with 40 to 80 units of the formulation of the present disclosure once or twice per week for up to 6 or 12 months.

In some aspects, the method includes treating a subject having edema with 40 to 80 units of the formulation of the present disclosure once or twice per week for up to 6 or 12 months, optionally in combination with a steroid, cyclophosphamide, mycophenolate, rituximab, alkylating agents, calcineurin inhibitors (e.g., cyclosporine, tacrolimus), angiotensin converting enzyme, and an angiotensin receptor blocker.

In some aspects, the method includes treating a subject having ulceratic colitis with 20, 40, or 80 units of the formulation of the present disclosure once or twice per week for 2 to 10 months, optionally in combination with one or more of a steroid, cyclosporine, tacrolimus, azathioprine, 6-mercaptopurine, Adalimumab, infliximab, vedolizumab, golimumab, and tofacitinib.

In some aspects, the method includes treating a subject having sarcoidosis with 40 to 80 units of the formulation of the present disclosure twice per week for up to 6 or 12 months, optionally in combination with one or more of a steroid, methotrexate, hydroxychloroquine, azathioprine, leflunomide, cyclophosphamide, mycophenolate, adalimumab, and infliximab.

In some aspects, the present disclosure includes testing a subject for at least one of the following conditions before administering the formulation of the present disclosure: scleroderma, osteoporosis, systemic fungal infections, ocular herpes simplex, recent surgery, history of or the presence of a peptic ulcer, congestive heart failure, hypertension, and sensitivity to proteins derived from porcine sources. In some aspects, the present disclosure includes testing a subject for at least one of the following conditions before administering the formulation of the present disclosure: primary adrenocortical insufficiency or adrenocortical hyperfunction. In some aspects, the present disclosure includes not administering the formulation of the present disclosure if the patient has any of the foregoing conditions. In some aspects, the present disclosure includes a dosage regimen wherein the subject is not administered any vaccines during dosing with the formulation of the present disclosure. In some aspects, the present disclosure includes a method of administering a vaccine at least 4 weeks prior to commencing administration of the formulation of the present disclosure. In some aspects, the vaccine may be a smallpox vaccine. In some aspects, the vaccine may be a mRNA vaccine. In some aspects, the vaccine may be protein vaccine.

In some aspects, the present disclosure includes a method of treating a subject having acute exacerbations of multiple sclerosis (MS) may comprise administering to the subject 40-80 USP units/ml of a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A, daily for 5-25 days, wherein the purified corticotropin is a naturally derived extract from a whole porcine pituitary gland including both anterior and posterior portions. In some aspects, the present disclosure includes a method of treating a subject having MS additionally with a steroid, IVIF, plasmaphoresis, alemtuzumab, ocrelizumab, mitoxantrone, natalizumab, fingolimod, peginterferon β-1a, dimethyl fumarate, monomethyl fumarate, teriflunomide, glatiramer acetate, IFN β-1a, IFN β-1b, and teriflunomide.

In some aspects, the present disclosure includes a method of treating a subject having acute gouty arthritis, severe psoriasis, atopic dermatitis, or allergic conjunctivitis, may comprise administering a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A to the subject, wherein the purified corticotropin is a naturally derived extract from a whole porcine pituitary gland including both anterior and posterior portions.

In some aspects, the present disclosure includes a method of treating a subject having acute gouty arthritis may comprise administering a sterile preparation of purified corticotropin and a second therapeutic agent to the subject, wherein the purified corticotropin is a naturally derived extract from a whole porcine pituitary gland including both anterior and posterior portions. In some aspects, the present disclosure includes further administering 3.5 to 7 mg prednisone daily to the subject.

In some aspects, the sterile preparation of purified corticotropin is administered daily for up to 5 days and the second therapeutic agent is administered daily for at least 7 days.

In some aspects, the purified corticotropin is administered in a first dose followed by one or more subsequent doses, and wherein the purified corticotropin comprises amino acids 1-39 of SEQ ID NO: 1.

In some aspects, the sterile preparation of the purified corticotropin is administered subcutaneously or intramuscularly.

In some aspects, 80-120 USP units/ml of purified corticotropin is administered daily for 2-3 weeks.

In some aspects, the present disclosure includes administering the sterile preparation of purified corticotropin comprises the steps of: withdrawing the sterile preparation from a vial with a first needle having a first gauge size with a first diameter, and injecting the sterile preparation into the subject with a second needle having a second gauge size with a second diameter.

In some aspects, the first diameter is wider than the second diameter. For example, the first gauge size is 20 G and the second gauge size is 23 G.

In some aspects, the vial is a sterile 5 mL multiple-dose vial containing 80 USP units/mL of the sterile preparation.

In some aspects, the method further includes the step of verifying adrenal responsiveness after administering the sterile preparation for a first time.

In some aspects, adrenal responsiveness is verified by a rise in urinary corticosteroid values and plasma corticosteroid values.

In some aspects, adrenal responsiveness is verified by administering 20 to 80 USP units/ml of the sterile preparation. In some aspects, the 20 to 80 USP units/ml of the sterile preparation is administered in a single injection or over a series of two or more injections.

In some aspects, the subject has a rise in urinary corticosteroid values and plasma corticosteroid values after administering the sterile preparation for a first time subcutaneously or intramuscularly.

In some aspects, the present disclosure includes a method of effecting a peak cortisol level of at least 30 micrograms/deciliter after 30 to 60 minutes of administration.

In some aspects, the sterile preparation of purified corticotropin is administered to the subject for more than one month, and the method further comprises administering corticosteroids to the subject. In some aspects, the method further comprises administering prednisone, methylprednisolone, and/or dexamethasone.

In some aspects, the subject is suspected to have a sensitivity to porcine protein, and the method further comprises performing skin testing prior to administering the sterile preparation and observing the subject for a reaction after administering the sterile preparation.

In some aspects, the subject is suspected to have an infection, and the method further comprises administering an appropriate anti-infective therapy.

In some aspects, the subject is pregnant with a child while administering the sterile preparation of purified corticotropin and the method further comprising observing the child for signs of hypoadrenalism.

In some aspects, the method includes storing the sterile preparation of purified corticotropin in the vial at 2° C. to 8° C., wherein the sterile preparation is a solid gel when stored, and warming the sterile preparation of purified corticotropin to a liquid gel before administering the sterile preparation.

In some aspects, the sterile preparation is warmed by rolling the vial between two hands for at least 2 minutes.

In some aspects, the vial comprise a top end with a cap and a rubber or silicone stopper, and the method further comprising removing the cap from the vial and wiping the stopper with a sterile alcohol wipe.

In some aspects, administering the sterile preparation of purified corticotropin comprises the steps of: withdrawing the sterile preparation from the vial with a first needle having a first gauge size with a first diameter, and injecting the sterile preparation into the individual with a second needle having a second gauge size with a second diameter.

In some aspects, the purified corticotropin comprises a polypeptide having an amino acid sequence of SYS-MEHFRWGKPVGKKRRPVKVYPNGAEDELAEAFPL-EF (SEQ ID NO: 1).

In some aspects a method of selecting a patient for treatment with a purified corticotropin injection may comprise measuring a first plasma corticosteroid level of the patient, administering a single injection of the purified corticotropin to the patient, measuring a second plasma corticosteroid level of the patient after the administering, selecting the patient for treatment if the second plasma corticosteroid level is higher than the first plasma corticosteroid level.

In some aspects, the method further includes: measuring a first urine corticosteroid level of the patient before step b) and measuring a second urine corticosteroid level of the patient after step b); and selecting the patient for treatment if the second urine corticosteroid level is higher than the first urine corticosteroid level.

In some aspects, the administering is subcutaneously or intramuscularly.

In some aspects, step b) comprises administering 80 (United States Pharmacopeia) USP units of the purified corticotropin to the patient. In some aspects, step b) comprises administering one or more injections of less than 80 USP units of the purified corticotropin to the patient. In some aspects, step b) comprises administering at least two injections of less than 80 USP units of the purified corticotropin to the patient.

In some aspects, the method further includes observing the site of injection after step b) for skin reactions.

In some aspects, the composition further comprises about 10-20% w/w gelatin, e.g., about 15% w/w gelatin. In some aspects, the composition further comprises about 0.1-1% w/w phenol, e.g., about 0.5% w/w phenol. In some aspects, the composition further comprises water for injection (WFI). In some aspects, the composition further comprises water for injection (WFI), gelatin, and phenol. In some aspects, the composition comprises water for injection (WFI), 15% w/w gelatin, and 0.5% w/w phenol.

In some aspects, the composition has not more than 0.05 USP Vasopressin Units/USP Corticotropin Units.

In some aspects, the patient is at risk of developing primary adrenal insufficiency or Addison's disease.

In some aspects, before purified cortrophin gel is administered via a route of treatment administration (i.e. intramuscularly or subcutaneously), adrenal responsiveness is verified using a route of verification administration that is the same route as the route of treatment administration. A rise in urinary and plasma corticosteroid values provides direct evidence of a stimulatory effect. Although corticotropin action is similar to that of exogenous adrenocortical steroids, a quantity of adrenocorticoid may be variable. In patients who receive prolonged corticotropin therapy, rapidly acting corticosteroids may be administered before, during and after an unusual stressful situation is indicated.

In some instances, the present disclosure includes methods of avoiding prolonged use of corticotropin that may produce posterior subcapsular cataracts and glaucoma with possible damage to the optic nerves. Corticotropin may mask some signs of infection, and new infections including those of the eye due to fungi or viruses may appear during its use.

In some instances, the present disclosure includes methods of restricting dietary salt, supplementing with potassium and/or calcium.

In some instances, the present disclosure includes observing patients with latent tuberculosis or tuberculin reactivity who receive corticotropin for reactivation of the disease and administering chemoprophylaxis to such patients.

In some instances, the present disclosure includes monitoring subjects after the administering for euphoria, insomnia, mood swings, personality changes, depression, and psychotic manifestations. In some instances, the present disclosure includes discontinuing the administering or reducing the dosage amount after detecting euphoria, insomnia, mood swings, personality changes, depression, and psychotic manifestations after the administering step.

In some instances, the present disclosure includes monitoring subjects after the administering for increased blood sugar, increased vascular constriction, reduced production of leukotrienes, reduced production of prostaglandins, inhibited white blood cell adhesion, blocked histamine release from mast cells, reduced number of eosinophils, blocked IL-2 production, reduced appetite, and/or decreased bone formation. In some instances, the present disclosure includes discontinuing the administering or reducing the dosage amount after detecting increased blood sugar, increased vascular constriction, reduced production of leukotrienes, reduced production of prostaglandins, inhibited white blood cell adhesion, blocked histamine release from mast cells, reduced number of eosinophils, blocked IL-2 production, reduced appetite, and/or decreased bone formation after the administering step.

In some instances, the present disclosure includes performing skin testing prior to treatment of patients with suspected sensitivity to porcine protein. In some aspects, immediately following intramuscular or subcutaneous administration of corticotropin, the present disclosure includes observing the patient's skin for sensitivity reactions.

In some instances, relative adrenocortical insufficiency induced by prolonged corticotropin therapy may be minimized by gradual reduction of corticotropin dosage. This type of insufficiency may persist for months after discontinuation of therapy; therefore, in any situation of stress during that period, hormone therapy may be reinstituted.

In some instances, the present disclosure includes adjusting the dose in patients with hypothyroidism and in those with cirrhosis, e.g., by reducing the dose.

In some aspects, the present disclosure includes a gradual reduction in dose administered, e.g., from 80 to 60 or 40 or 20 USP units per dose.

In some instances, corticotropin may be administered for treatment only when the disease is intractable to first line therapies. In some instances, corticotropin may be adjunctive in the treatment of a disease.

In some instances, maximal corticotropin stimulation of the adrenals may be limited during the first few days of treatment. Accordingly, other drugs may be administered when an immediate therapeutic effect is desirable.

If an infection is present, appropriate anti-infective therapy may be administered during treatment with corticotropin and following discontinuation of corticotropin therapy.

In some instances, treatment of acute gouty arthritis may be limited to a few days. Since rebound attacks may occur when corticotropin is discontinued, conventional concomitant therapy may be administered during corticotropin treatment of the present disclosure, and for several days after it is stopped.

In some instances, the present disclosure includes observing patients with diabetes, abscess, pyogenic infections, diverticulitis, renal insufficiency, and myasthenia gravis after administering the formulation of the present disclosure. In some instances, the present disclosure includes observing patients with hypoprothrombinemia after administering the formulation of the present disclosure in conjunction with aspirin and discontinuing administration of the aspirin if the subject exhibits adverse side effects upon such administering.

In some instances, the present disclosure includes observing growth and development of infants and children on prolonged corticotropin therapy.

In some instances, the present disclosure includes avoiding administration of aspirin.

In some instances, the present disclosure includes administering an intramuscular injection of 80 Units of cortrophin gel and achieving a reach peak cortisol concentration in 5-10 hours. In some aspects, the present disclosure includes administering an intramuscular injection of 80 Units of cortrophin gel to obtain a maximum (CV %) cortisol levels of about 30-38 µg/dL, 32-36 µg/dL, or 34-35 µg/dL.

In some aspects, a method of storing and warming a sterile corticotropin composition may comprise storing the sterile corticotropin composition in a multiple-dose vial comprising 80 USP units/mL of the sterile corticotropin composition, wherein the vial comprises a rubber stopper coated with cross-linked silicones, at a temperature of 2° to 8° C.; and warming the vial to a temperature of 18° to 26° C.

In some aspects, the sterile corticotropin composition has physical properties such that it is a solid gel at 2° to 8° C. and is a liquid gel at 18° to 26° C.

In some aspects, step c) comprises rolling the vial between two hands for at least two minutes.

In some aspects, the sterile corticotropin composition further comprises 0.5% phenol, 15.0% gelatin, water, hydrochloric acid, and sodium hydroxide.

In some aspects, the sterile corticotropin composition has a pH of 3.0-7.0.

In some aspects, the corticotropin comprises amino acids 1-39 of SEQ ID NO: 1.

In some aspects, the corticotropin is a naturally derived extract from a whole porcine pituitary gland including both anterior and posterior portions.

In some aspects, the stopper comprises a coating comprising silicone oils of different molecule weights.

In some aspects, the multiple-dose vial further comprises a removable cap covering the stopper.

In some aspects, the multiple-dose vial has a diameter of 13 mm.

In some aspects, the multiple-dose vial comprises an aluminum seal.

The method of claim 10, wherein the removable cap has a diameter of 13 mm.

In some aspects, the multiple-dose vial is borosilicate USP Type I glass.

In some aspects, the sterile corticotropin composition is in the form of a composition containing 0.05 to 0.2% of the purified corticotropin.

In some aspects, the sterile corticotropin composition further comprises about 10-20% w/w or about 15% gelatin.

In some aspects, the composition further comprises about 0.1-1% or about 0.5% w/w phenol.

In some aspects, the sterile corticotropin composition further comprises water for injection (WFI). In some aspects, the sterile corticotropin composition further comprises water for injection (WFI), gelatin, and phenol.

In some aspects, the sterile corticotropin composition comprises water for injection (WFI), 15% w/w gelatin, and 0.5% w/w phenol.

In some aspects, the sterile corticotropin composition has not more than 0.05 USP Vasopressin Units/USP Corticotropin Units.

Method of Manufacturing

In some aspects, a method of manufacturing a sterile preparation of purified corticotropin, comprising extracting corticotropin from a whole porcine pituitary gland including both anterior and posterior portions, and removing proteins or peptides having a molecular weight higher than ACTH.

In some aspects, the purified corticotropin comprises a polypeptide having an amino acid sequence of SYSMEHFRWGKPVGKKRRPVKVYPNGAEDELAEAFPLEF (SEQ ID NO: 1).

In some aspects, the method further comprising analyzing the sample using reversed-phase High Performance Liquid Chromatography (RP-HPLC).

In some aspects, the method further includes subjecting the sterile preparation to sodium dodecyl sulfate-polyacrylamide gel electrophoresis (SDS-PAGE) or Western blotting and identifying impurities.

In some aspects, the method does not include a terminal sterilization process.

In some aspects, the sterile preparation of purified corticotropin comprises 0.5% w/w phenol, 15.0% w/w gelatin, and water for injection (WFI).

In some aspects, the method further includes adjusting pH of the sterile preparation with hydrochloric acid and sodium hydroxide.

In some aspects, the sterile preparation has a pH of 3.0-7.0.

In some aspects, the sterile corticotropin composition further comprises about 150 mg/ml gelatin.

In some aspects, the gelatin is Type A gelatin.

In some aspects, the sterile preparation of purified corticotropin comprises 20 to 100 USP units/mL of purified corticotropin powder.

In some aspects, the sterile preparation of purified corticotropin comprises 40 to 100 USP units/mL of purified corticotropin powder.

In some aspects, the sterile preparation of purified corticotropin comprises 80 USP units/mL of purified corticotropin powder.

In some aspects, the sterile preparation of purified corticotropin comprises trace amounts of hydrochloric acid and sodium hydroxide.

Methods of Testing

In some aspects, a method of testing a sterile preparation of purified corticotropin for safety may comprise testing the sterile preparation of purified corticotropin using quantitative polymerase chain reaction (qPCR), and performing forced degradation of the sterile preparation under acidic, basic, thermal, photolytic, and/or oxidative stress conditions to produce a sample.

In some aspects, the method further includes analyzing the sample using reversed-phase High Performance Liquid Chromatography (RP-HPLC).

In some aspects, the method further includes subjecting the sterile preparation to sodium dodecyl sulfate-polyacrylamide gel electrophoresis (SDS-PAGE) or Western blotting and identifying impurities.

In some aspects, the sterile preparation of purified corticotropin comprises 80 USP units/mL of the sterile preparation, 0.5% w/w phenol, 15.0% w/w gelatin, water for injection (WFI).

In some aspects, the corticotropin comprises amino acids 1-39 of SEQ ID NO: 1.

In some aspects, the corticotropin is a naturally derived extract from a whole porcine pituitary gland including both anterior and posterior portions.

In some aspects, the method further includes verifying that the sample has not more than 0.05 USP Vasopressin Units/USP Corticotropin Units.

Kits

In some aspects, the present disclosure includes a kit including a vial containing a sterile preparation of purified corticotropin, a first needle having a first gauge size with a first diameter, and a second needle having a second gauge size with a second diameter, wherein the sterile preparation comprises 80 USP units per mL of corticotropin, phenol, type A gelatin, water for injection (WFI), hydrochloric acid, and sodium hydroxide, wherein the vial is not terminally sterilized.

The kit may include instructions for use according to the present disclosure. In some aspects, the instructions may include washing hands thoroughly and drying with a clean towel, removing the vial from a refrigerator, confirming that the expiration date has not passed, warming the gel in the vial from a solid gel to a liquid gel by rolling between hands for at least one minute, removing plastic cap from the top of the vial, wiping top of the vial stopper with a sterile alcohol wipe, using a sterile 20 G needle and syringe to draw up the warmed purified cortrophin gel from the vial, removing the 20 G needle, attaching a 23 G needle to the syringe, injecting the warmed purified cortrophin gel from the syringe into the subject.

In some aspects, the vial is a 5 mL multiple-dose vial.

In some aspects, the first diameter is wider than the second diameter.

In some aspects, the first gauge size is 20 G and the second gauge size is 23 G.

In some aspects, the sterile preparation comprises 0.5% w/w phenol, 15.0% w/w gelatin, and water for injection (WFI).

In some aspects, the sterile preparation comprises trace amounts of hydrochloric acid and sodium hydroxide.

In some aspects, the sterile preparation has a pH of 3.0-7.0.

In some aspects, the sterile preparation comprises 0.5% w/w phenol, 15.0% w/w gelatin, and water for injection (WFI).

In some aspects, the sterile preparation comprises about 0.05 to 0.2% of the purified corticotropin.

In some aspects, the sterile preparation further comprises about 10-20% w/w gelatin.

In some aspects, the sterile preparation further comprises about 15% w/w gelatin.

In some aspects, the sterile preparation further comprises about 150 mg/ml gelatin.

In some aspects, the sterile preparation further comprises about 0.1-1% w/w phenol.

In some aspects, the sterile preparation further comprises about 0.5% w/w phenol.

In some aspects, sterile preparation further comprises about 5 mg/ml phenol.

In some aspects, the sterile preparation of purified corticotropin comprises 20 to 80 USP units/mL of purified corticotropin powder.

In some aspects, the sterile preparation of purified corticotropin comprises 40 to 80 USP units/mL of purified corticotropin powder.

In some aspects, the sterile preparation of purified corticotropin comprises 80 USP units/mL of purified corticotropin powder.

In some aspects, the purified corticotropin comprises a polypeptide having an amino acid sequence of SYSMEHFRWGKPVGKKRRPVKVYPNGAEDELAEAFPLEF (SEQ ID NO: 1).

Dosage and Administration

In some aspects, the method of administering a sterile corticotropin composition to a human subject may comprise (a) warming a vial containing the sterile corticotropin composition from a temperature of 2° to 8° C. to a temperature of 18° to 26° C.; (b) withdrawing the sterile corticotropin composition from the vial with a first needle having a first gauge size with a first diameter; (c) replacing the first needle with a second needle having a second gauge size with a second diameter that is different from the first diameter; (d) and injecting the sterile preparation into the subject thereof with the second needle.

In some aspects, the warming is performed in a range of 30 seconds to 3 minutes.

In some aspects, step a) comprises rolling the vial between two hands.

In some aspects, the injecting is subcutaneously or intramuscularly.

In some aspects, step d) comprises injecting 80 (United States Pharmacopeia) USP units of the sterile corticotropin composition to the patient. In some aspects, step d) comprises injecting one or more injections of less than 80 USP units of the sterile corticotropin composition to the patient.

In some aspects, step d) comprises injecting at least two injections of less than 80 USP units of the sterile corticotropin composition to the patient. In some aspects, the method further includes observing the site of injection after step d) for skin reactions.

In some aspects, steps a)-d) are repeated daily for up to 5 days and the second therapeutic agent is administered daily for at least 7 days.

In some aspects, steps a)-d) are repeated daily for 2-3 weeks, wherein step d) comprises injecting 80-120 USP units/ml of purified corticotropin.

In some aspects, the sterile corticotropin composition is in the form of a composition containing 0.05 to 0.2% of the purified corticotropin. In some aspects, the sterile corticotropin composition further comprises about or about 15% w/w gelatin.

In some aspects, the composition further comprises about or about 0.5% w/w phenol.

In some aspects, the sterile corticotropin composition further comprises water for injection (WFI). In some aspects, the sterile corticotropin composition further comprises water for injection (WFI), gelatin, and phenol. In some aspects, the sterile corticotropin composition comprises water for injection (WFI), 15% w/w gelatin, and 0.5% w/w phenol.

In some aspects, the sterile corticotropin composition has not more than 0.05 USP Vasopressin Units/USP Corticotropin Units.

In some aspects, the method further includes administering a second therapeutic agent to the subject. In some aspects, the method further includes administering a rapidly acting corticosteroid to the subject.

In some aspects, the vial is a sterile 5 mL multiple-dose vial comprising 80 USP units/mL of the sterile corticotropin composition.

In some aspects, the method further includes verifying a rise in urinary corticosteroid values and plasma corticosteroid values after step d), wherein step d) comprises injecting 20 to 80 USP units/ml of the sterile corticotropin composition.

In some aspects, the method further includes administering an anti-infective drug.

In some aspects, the subject is pregnant with a child during the administering and the method further comprises observing the child for signs of hypoadrenalism.

In some aspects, the sterile corticotropin composition is a solid gel before step a), and the sterile preparation is a liquid gel after step a).

In some aspects, the vial comprises a top opening, a rubber stopper sealing the top opening, and a cap covering the top opening, and the method further comprises removing the cap from the vial and wiping the rubber stopper with a sterile alcohol wipe.

In some aspects, the method further includes preparing an injection site of a subject by wiping the subject's skin with a sterile alcohol wipe and air drying the injection site before performing step d).

In some instances, tests for verification of adrenal responsiveness to corticotropin may utilize as much as 80 units as a single injection or one or more injections of a lesser dosage. Verification tests may be performed prior to treatment with corticotropins. The test may utilize the route of treatment administration proposed for treatment. Following verification, dosage may be individualized according to the disease under treatment and the general medical condition of each patient.

In some instances, frequency and dose of the drug may be determined by considering severity of the disease, plasma and urine corticosteroid levels and the initial response of the patient. Only gradual change in dosage schedules may be attempted, after full drug effects have become apparent. In some instances, treatment of acute exacerbations of multiple sclerosis may include daily intramuscular doses of 80-120 units for 2-3 weeks.

In some instances, the chronic administration of more than 40 units daily may be associated with uncontrollable adverse effects. In some aspects, the present disclosure includes recuding the administered dosage gradually by either reducing the amount of each injection, or administering injections at longer intervals, or both.

Instructions for Use

During storage, the purified cortrophin gel of the present disclosure is a solid gel.

FIG. 1 depicts aspects of one embodiment of a method of administering the purified cortrophin gel. In some instances, it needs to be warmed to a liquid gel before injecting. As shown in FIG. 1(a), the contents of the vial may be warmed by rolling between hands for a few minutes. In some instances, the contents of the vial is not microwaved or heated on the stove.

As depicted in FIG. 1(b), in some instances, the plastic cap is removed (e.g., flipped off) from the top of the purified Cortrophin Gel vial and thrown away in the trash. In some instances, the plastic cap is not put back on the vial.

As shown in FIG. 1(c), the top of the vial rubber stopper is wiped with a new sterile alcohol wipe.

As depicted in FIG. 1(d), a new sterile 20 G needle (or needle prescribed for withdrawal) and syringe may be used to draw up a needed amount of the purified Cortrophin Gel.

In some instances, the skin is prepared at an injection site by wiping the skin at the injection site with a new sterile alcohol wipe. In some instances, the skin at the injection site is allowed to air dry.

In some instances, the 20 G needle used for drawing the purified cortrophin gel from the vial is replaced with the 23 G needle.

In some aspects, the present disclosure includes a method of using a sterile preparation of purified corticotropin, may comprise administering a sterile preparation of purified corticotropin to an individual in need thereof, wherein administering the sterile preparation of purified corticotropin comprises the steps of: withdrawing the sterile preparation from a vial with a first needle having a first gauge size with a first diameter, and injecting the sterile preparation into the individual with a second needle having a second gauge size with a second diameter. In some aspects, the first diameter is wider than the second diameter. In some aspects, the first gauge size is 20 G and the second gauge size is 23 G. In some aspects, the 20 to 80 USP units/mL of the sterile preparation is administered in a single injection or over a series of two or more injections.

In some aspects, the method further includes verifying adrenal responsiveness after injection. In some aspects, adrenal responsiveness is verified by a rise in urinary corticosteroid values and plasma corticosteroid values. In some aspects, adrenal responsiveness is verified by administering 20 to 80 USP units/mL of the sterile preparation.

In some aspects, the individual has a rise in urinary corticosteroid values and plasma corticosteroid values after administering the sterile preparation for a first time subcutaneously or intramuscularly.

In some aspects, the sterile preparation of purified corticotropin is administered to the individual for a prolonged period of time, and the method further comprises administering rapidly acting corticosteroids before, during or after an unusual stressful situation.

Storage and Handling

In some aspects, the present disclosure includes providing the purified cortrophin gel in 5 mL multiple-dose vials containing 80 USP units/mL and storing at between 36° F. to 46° F. (2° C. to 8° C.).

In some aspects, the present disclosure includes a vial containing a filter-sterilized preparation of purified corticotropin may comprise 80 USP units per mL of corticotropin, 0.5% w/w phenol, 15.0% w/w gelatin, water for injection (WFI), wherein the gelatin is Type A, wherein the vial is not terminally sterilized. In some aspects, the preparation further includes sodium hydroxide and/or hydrochloric acid.

In some aspects, the filter-sterilized preparation has a pH of 3.0-7.0.

In some aspects, the purified corticotropin comprises amino acids 1-39 of SEQ ID NO: 1.

In some aspects, the purified corticotropin comprises an extract from whole porcine pituitary gland including both anterior and posterior portions of the whole porcine pituitary gland.

In some aspects, the phenol is multi-compendial grade phenol.

In some aspects, the vial is a multiple-dose vial comprising a stopper. In some aspects, the comprises a rubber stopper coated with cross-linked silicones. In some aspects, the stopper comprises a coating comprising silicone oils of different molecule weights.

In some aspects, the multiple-dose vial is a 5 mL multiple-dose vial. In some aspects, the multiple-dose vial further comprises a removable cap covering the stopper.

In some aspects, the multiple-dose vial has a diameter of 13 mm. In some aspects, the multiple-dose vial comprises an aluminum seal. The vial of claim 17, wherein the removable cap has a diameter of 13 mm. In some aspects, the multiple-dose vial is borosilicate USP Type I glass. In some aspects, the filter-sterilized preparation has not more than 0.05 USP Vasopressin Units/USP Corticotropin Units.

In some aspects, the vial further comprising 80 U/ml purified corticotropin powder, 150 mg/ml type A gelatin, 5 mg/ml phenol, hydrochloric acid, sodium hydroxide, and 1 ml water for injection.

In some aspects, the gelatin has a pH of 5.9 to 6.2.

In some aspects, the filter-sterilized preparation has less than 6000 particles greater than or equal to 10 μm.

In some aspects, the filter-sterilized preparation has less than 600 particles greater than or equal to 25 μm.

In some aspects, the filter-sterilized preparation is free of acetic acid.

In some aspects, the filter-sterilized preparation of purified corticotropin is a prolonged release formulation.

This disclosure also includes the following non-limiting numbered aspects:

A method of manufacturing a sterile preparation of purified corticotropin, comprising:
 extracting corticotropin from a whole porcine pituitary gland including both anterior and posterior portions, and
 removing proteins or peptides having a molecular weight higher than ACTH.

The method of numbered aspect 1, wherein the purified corticotropin comprises a polypeptide having an amino acid sequence of (SEQ ID NO: 1)
SYSMEHFRWGKPVGKKRRPVKVYPNGAEDELAEAFPLEF.

The method of numbered aspect 1 or numbered aspect 2, further comprising performing forced degradation of the sterile preparation under acidic, basic, thermal, photolytic, and/or oxidative stress conditions to produce a sample.

The method of any one of numbered aspects 1-3, further comprising analyzing the sample using reversed-phase High Performance Liquid Chromatography (RP-HPLC).

The method of any one of numbered aspects 1-4, further comprising subjecting the sterile preparation to sodium dodecyl sulfate-polyacrylamide gel electrophoresis (SDS-PAGE) or Western blotting and identifying impurities.

The method of any one of numbered aspects 1-5, further comprising removing porcine genomic DNA and testing the sterile preparation of purified corticotropin using quantitative polymerase chain reaction (qPCR).

The method of any one of numbered aspects 1-6, wherein the method does not include a terminal sterilization process.

The method of any one of numbered aspects 1-7, wherein the sterile preparation of purified corticotropin comprises 0.5% w/w phenol, 15.0% w/w gelatin, and water for injection (WFI).

The method of any one of numbered aspects 1-8, further comprising adjusting pH of the sterile preparation with hydrochloric acid and sodium hydroxide.

The method of any one of numbered aspects 1-9, wherein the sterile preparation has a pH of 3.0-7.0.

The method of any one of numbered aspects 1-10, wherein the sterile corticotropin composition further comprises about 150 mg/ml gelatin.

The method of any one of numbered aspects 1-11, wherein the gelatin is Type A gelatin.

The method of any one of numbered aspects 1-12, wherein the sterile preparation of purified corticotropin comprises 20 to 100 USP units/mL of purified corticotropin powder.

The method of any one of numbered aspects 1-13, wherein the sterile preparation of purified corticotropin comprises 40 to 100 USP units/mL of purified corticotropin powder.

The method of any one of numbered aspects 1-14, wherein the sterile preparation of purified corticotropin comprises 80 USP units/mL of purified corticotropin powder.

The method of any one of numbered aspects 1-15, wherein the sterile preparation of purified corticotropin comprises trace amounts of hydrochloric acid and sodium hydroxide.

The method of any one of numbered aspects 1-16, wherein the sterile preparation of purified corticotropin is preservative-free, antimicrobial-free, or both.

A method of storing and warming a sterile corticotropin composition, comprising:
 storing the sterile corticotropin composition in a multiple-dose vial comprising 80 USP units/mL of the sterile corticotropin composition, wherein the vial comprises a rubber stopper coated with cross-linked silicones, at a temperature of 2° to 8° C.; and
 warming the vial to a temperature of 18° to 26° C.

The method of numbered aspect 18, wherein the sterile corticotropin composition has physical properties such that it is a solid gel at 2° to 8° C. and is a liquid gel at 18° to 26° C.

The method of numbered aspect 18 or numbered aspect 19, wherein step b) comprises rolling the vial between two hands for at least two minutes.

The method of any one of numbered aspects 18-20, wherein the sterile corticotropin composition further comprises 0.5% phenol, 15.0% gelatin, water, hydrochloric acid, and sodium hydroxide.

The method of any one of numbered aspects 18-21, wherein the sterile corticotropin composition has a pH of 3.0-7.0.

The method of any one of numbered aspects 18-22, wherein the corticotropin comprises amino acids 1-39 of SEQ ID NO: 1.

The method of any one of numbered aspects 18-23, wherein the corticotropin is a naturally derived extract from a whole porcine pituitary gland including both anterior and posterior portions.

The method of any one of numbered aspects 18-24, wherein the stopper comprises a coating comprising silicone oils of different molecule weights including polydimethylsiloxane such as B2 coating.

The method of any one of numbered aspects 18-25, wherein the multiple-dose vial is a 5 mL multiple-dose vial.

The method of any one of numbered aspects 18-26, wherein the multiple-dose vial further comprises a removable cap covering the stopper.

The method of any one of numbered aspects 18-27, wherein the multiple-dose vial has a diameter of 13 mm.

The method of any one of numbered aspects 18-28, wherein the multiple-dose vial comprises an aluminum seal.

The method of numbered aspect 27, wherein the removable cap has a diameter of 13 mm.

The method of any one of numbered aspects 18-30, wherein the multiple-dose vial is borosilicate USP Type I glass.

The method of any one of numbered aspects 18-31, wherein the sterile corticotropin composition is in the form of a composition containing 0.05 to 0.2% of the purified corticotropin.

The method of any one of numbered aspects 18-32, wherein the sterile corticotropin composition further comprises about 10-20% w/w gelatin.

The method of any one of numbered aspects 18-33, wherein the sterile corticotropin composition further comprises about 15% w/w gelatin.

The method of any one of numbered aspects 18-34, wherein the composition further comprises about 0.1-1% w/w phenol.

The method of any one of numbered aspects 18-35, wherein the sterile corticotropin composition further comprises about 0.5% w/w phenol.

The method of any one of numbered aspects 18-36, wherein the sterile corticotropin composition further comprises water for injection (WFI).

The method of any one of numbered aspects 18-37, wherein the sterile corticotropin composition further comprises water for injection (WFI), gelatin, and phenol.

The method of any one of numbered aspects 18-38, wherein the sterile corticotropin composition comprises water for injection (WFI), 15% w/w gelatin, and 0.5% w/w phenol.

The method of any one of numbered aspects 18-39, wherein the sterile corticotropin composition has not more than 0.05 USP Vasopressin Units/USP Corticotropin Units.

A vial containing a filter-sterilized preparation of purified corticotropin comprising 80 USP units per mL of corticotropin, 0.5% w/w phenol, 15.0% w/w gelatin, water for injection (WFI), hydrochloric acid, and sodium hydroxide, wherein the gelatin is Type A, wherein the vial is not terminally sterilized.

The vial of numbered aspect 41, wherein the filter-sterilized preparation has a pH of 3.0-7.0.

The vial of numbered aspect 41 or numbered aspect 42, wherein the purified corticotropin comprises amino acids 1-39 of SEQ ID NO: 1.

The vial of any one of numbered aspects 41-43, wherein the purified corticotropin comprises an extract from whole porcine pituitary gland including both anterior and posterior portions of the whole porcine pituitary gland, and wherein the filter-sterilized preparation has not more than 0.05 USP Vasopressin Units/USP Corticotropin Units.

The vial of any one of numbered aspects 41-44, wherein the phenol is multi-compendial grade phenol.

The vial of any one of numbered aspects 41-45, wherein the vial is a multiple-dose vial comprising a stopper.

The vial of numbered aspect 46, wherein the stopper is coated with cross-linked silicones.

The vial of numbered aspect 46, wherein the stopper comprises a coating comprising silicone oils of different molecule weights including polydimethylsiloxane such as B2 coating.

The vial of any one of numbered aspects 46-48, wherein the multiple-dose vial is a 5 mL multiple-dose vial.

The vial of any one of numbered aspects 46-49, wherein the multiple-dose vial further comprises a removable cap covering the stopper.

The vial of any one of numbered aspects 46-50, wherein the multiple-dose vial has a diameter of 13 mm.

The vial of any one of numbered aspects 46-51, wherein the multiple-dose vial comprises an aluminum seal.

The vial of numbered aspect 50, wherein the removable cap has a diameter of 13 mm.

The vial of any one of numbered aspects 46-53, wherein the multiple-dose vial is borosilicate USP Type I glass.

The vial of any one of numbered aspects 46-54, further comprising about 1 mg/ml purified corticotropin powder, 150 mg/ml type A gelatin, 5 mg/ml phenol, hydrochloric acid, sodium hydroxide, and 1 ml water for injection.

The vial of any one of numbered aspects 46-55, wherein the gelatin has a pH of 5.9 to 6.2.

The vial of any one of numbered aspects 46-56, wherein the filter-sterilized preparation has less than 6000 particles ≥10 μm.

The vial of any one of numbered aspects 46-57, wherein the filter-sterilized preparation has less than 600 particles ≥25 μm.

The vial of any one of numbered aspects 46-58, wherein the filter-sterilized preparation is free of acetic acid.

The vial of any one of numbered aspects 46-59, wherein the filter-sterilized preparation of purified corticotropin is a prolonged release formulation.

The vial of any one of numbered aspects 46-60, wherein the gelatin is pyrogen-free.

The vial of any one of numbered aspects 46-61, comprising acidified WFI having a pH of 2.8 to 3.2.

The vial of any one of numbered aspects 41-62, wherein the filter-sterilized preparation of purified corticotropin is preservative-free, antimicrobial-free, or both.

A method of treating a subject having acute exacerbations of multiple sclerosis (MS) comprising administering to the subject 40-80 USP units/ml of a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A, daily for 5-25 days, wherein the purified corticotropin is a naturally derived extract from a whole porcine pituitary gland including both anterior and posterior portions.

A method of treating a subject having acute gouty arthritis, severe psoriasis, atopic dermatitis, or allergic conjunctivitis, comprising administering a filter-sterilized preparation of purified corticotropin comprising 80 USP units per mL of corticotropin, 0.5% w/w phenol, 15% w/w gelatin, water for injection (WFI), hydrochloric acid, and sodium hydroxide, wherein the gelatin is Type A to the subject, wherein the purified corticotropin is a naturally derived extract from a whole porcine pituitary gland including both anterior and posterior portions.

A method of treating a subject having acute gouty arthritis comprising administering a sterile preparation of purified corticotropin and a second therapeutic agent to the subject, wherein the purified corticotropin is a naturally derived extract from a whole porcine pituitary gland including both anterior and posterior portions.

The method of any one of numbered aspects 64-66, wherein the sterile preparation of purified corticotropin is administered daily for up to 5 days and the second therapeutic agent is administered daily for at least 7 days.

The method of any one of numbered aspects 64-67, wherein the purified corticotropin is administered in a first dose followed by one or more subsequent doses, and wherein the purified corticotropin comprises amino acids 1-39 of SEQ ID NO: 1.

The method of any one of numbered aspects 64-68, wherein the sterile preparation of the purified corticotropin is administered subcutaneously or intramuscularly.

The method of any one of numbered aspects 64-69, wherein 80-120 USP units/ml of purified corticotropin is administered daily for 2-3 weeks.

The method of any one of numbered aspects 64-70, wherein administering the sterile preparation of purified corticotropin comprises the steps of: withdrawing the sterile preparation from a vial with a first needle having a first gauge size with a first diameter, and injecting the sterile preparation into the subject with a second needle having a second gauge size with a second diameter.

The method of numbered aspect 71, wherein the first diameter is wider than the second diameter.

The method of numbered aspect 71 or numbered aspect 72, wherein the first gauge size is 20 G and the second gauge size is 23 G.

The method of any one of numbered aspects 71-73, wherein the vial is a sterile 5 mL multiple-dose vial containing 80 USP units/mL of the sterile preparation.

The method of any one of numbered aspects 64-74, further comprising the step of verifying adrenal responsiveness after administering the sterile preparation for a first time.

The method of numbered aspect 75, wherein adrenal responsiveness is verified by a rise in urinary corticosteroid values and plasma corticosteroid values.

The method of numbered aspect 76, wherein adrenal responsiveness is verified by administering 20 to 80 USP units/ml of the sterile preparation.

The method of numbered aspect 77, wherein the 20 to 80 USP units/ml of the sterile preparation is administered in a single injection or over a series of two or more injections.

The method of any one of numbered aspects 64-78, wherein the subject has a rise in urinary corticosteroid values and plasma corticosteroid values after administering the sterile preparation for a first time subcutaneously or intramuscularly.

The method of any one of numbered aspects 64-79, wherein the sterile preparation of purified corticotropin is administered to the subject for more than one month, and the method further comprises administering corticosteroids to the subject.

The method of any one of numbered aspects 64-80, wherein the subject is suspected to have a sensitivity to porcine protein, and the method further comprises performing skin testing prior to administering the sterile preparation and observing the subject for a reaction after administering the sterile preparation.

The method of any one of numbered aspects 64-81, wherein the subject is suspected to have an infection, and the method further comprises administering an appropriate anti-infective therapy.

The method of any one of numbered aspects 64-82, wherein the subject is pregnant with a child while administering the sterile preparation of purified corticotropin and the method further comprising observing the child for signs of hypoadrenalism.

The method of any one of numbered aspects 64-83, comprising storing the sterile preparation of purified corticotropin in the vial at 2° C. to 8° C., wherein the sterile preparation is a solid gel when stored, and warming the sterile preparation of purified corticotropin to a liquid gel before administering the sterile preparation.

The method of any one of numbered aspects 64-84, wherein the sterile preparation is warmed by rolling the vial between two hands for at least 2 minutes.

The method of any one of numbered aspects 71-85, wherein the vial comprises a top end with a cap and a rubber or silicone stopper, and the method further comprising removing the cap from the vial and wiping the stopper with a sterile alcohol wipe.

The method of any one of numbered aspects 64-86, wherein administering the sterile preparation of purified corticotropin comprises the steps of: withdrawing the sterile preparation from the vial with a first needle having a first gauge size with a first diameter, and injecting the sterile preparation into the individual with a second needle having a second gauge size with a second diameter.

The method of any one of numbered aspects 64-87, wherein the purified corticotropin comprises a polypeptide having an amino acid sequence of (SEQ ID NO: 1)
SYSMEHFRWGKPVGKKRRPVKVYPNGAEDELAEAFPLEF.

A method of testing a sterile preparation of purified corticotropin for safety comprising testing the sterile preparation of purified corticotropin using quantitative polymerase chain reaction (qPCR), and performing forced degradation of the sterile preparation under acidic, basic, thermal, photolytic, and/or oxidative stress conditions to produce a sample.

The method of numbered aspect 89, further comprising analyzing the sample using reversed-phase High Performance Liquid Chromatography (RP-HPLC).

The method of numbered aspect 89 or numbered aspect 90, further comprising subjecting the sterile preparation to sodium dodecyl sulfate-polyacrylamide gel electrophoresis (SDS-PAGE) or Western blotting and identifying impurities.

The method of any one of numbered aspects 89-91, wherein the sterile preparation of purified corticotropin comprises 80 USP units/mL of the sterile preparation, 0.5% w/w phenol, 15.0% w/w gelatin, water for injection (WFI).

The method of any one of numbered aspects 89-92, wherein the corticotropin comprises amino acids 1-39 of SEQ ID NO: 1.

The method of any one of numbered aspects 89-93, wherein the corticotropin is a naturally derived extract from a whole porcine pituitary gland including both anterior and posterior portions.

The method of any one of numbered aspects 89-94, further comprising verifying that the sample has not more than 0.05 USP Vasopressin Units/USP Corticotropin Units.

The method of any one of numbered aspects 90-95, wherein the filter-sterilized preparation of purified corticotropin is preservative-free, antimicrobial-free, or both.

A kit comprising a vial containing a filter-sterilized preparation of purified corticotropin, a first needle having a first gauge size with a first diameter, and a second needle having a second gauge size with a second diameter, wherein the sterile preparation comprises 80 USP units per mL of corticotropin, phenol, type A gelatin, water for injection (WFI), hydrochloric acid, and sodium hydroxide, wherein the vial is not terminally sterilized.

The kit of numbered aspect 97, wherein the vial is a 5 mL multiple-dose vial.

The kit of numbered aspect 97 or numbered aspect 98, wherein the first diameter is wider than the second diameter.

The kit of any one of numbered aspects 97-99, wherein the first gauge size is 20 G and the second gauge size is 23 G.

The kit of any one of numbered aspects 97-100, wherein the filter-sterilized preparation comprises 0.5% w/w phenol, 15.0% w/w gelatin, and water for injection (WFI).

The kit of any one of numbered aspects 97-101, wherein the filter-sterilized preparation comprises trace amounts of hydrochloric acid and sodium hydroxide.

The kit of any one of numbered aspects 97-102, wherein the filter-sterilized preparation has a pH of 3.0-7.0.

The kit of any one of numbered aspects 97-103, wherein the filter-sterilized preparation comprises 0.5% w/w phenol, 15.0% w/w gelatin, and water for injection (WFI).

The kit of any one of numbered aspects 97-103, wherein the filter-sterilized preparation further comprises about 15% w/w gelatin.

The kit of any one of numbered aspects 97-103, wherein the filter-sterilized preparation further comprises about 150 mg/ml gelatin.

The kit of any one of numbered aspects 97-103, wherein the filter-sterilized preparation further comprises about 0.1-1% w/w phenol.

The kit of numbered aspect 107, wherein the filter-sterilized preparation further comprises about 0.5% w/w phenol.

The kit of numbered aspect 106, wherein filter-sterilized preparation further comprises about 5 mg/ml phenol.

The kit of any one of numbered aspects 97-109, wherein the filter-sterilized preparation of purified corticotropin comprises 20 to 80 USP units/mL of purified corticotropin powder.

The kit of any one of numbered aspects 97-110, wherein the filter-sterilized preparation of purified corticotropin comprises 40 to 80 USP units/mL of purified corticotropin powder.

The kit of any one of numbered aspects 97-111, wherein the filter-sterilized preparation of purified corticotropin comprises 80 USP units/mL of purified corticotropin powder.

The kit of any of any one of numbered aspects 97-112, wherein the purified corticotropin comprises a polypeptide having an amino acid sequence of (SEQ ID NO: 1)
SYSMEHFRWGKPVGKKRRPVKVYPNGAEDELAEAFPLEF.

The kit of any of any one of numbered aspects 97-113, wherein the filter-sterilized preparation of purified corticotropin is preservative-free, antimicrobial-free, or both.

The kit of any one of numbered aspects 97-114, wherein the kit further comprises instructions for use including washing hands and drying with a clean towel, removing the vial from a refrigerator, confirming that an expiration date on the vial has not passed, warming the gel in the vial from a solid gel to a liquid gel by rolling between hands for at least one minute, removing plastic cap from the top of the vial, wiping top of the vial stopper with a sterile alcohol wipe, using a sterile 20 G needle and syringe to draw up the warmed purified cortrophin gel from the vial, removing the 20 G needle, attaching a 23 G needle to the syringe, injecting the warmed purified cortrophin gel from the syringe into the subject.

Example 1

Using multiple analytical techniques, two extractable/leachable studies of the primary container closure system for the sterile preparation of purified corticotropin were performed. Samples of the extracts of product contact components were tested for volatile organic extractables, semi-volatile organic extractables, non-volatile organic extractables, and inorganic extractables. The analytical evaluation threshold (AET) was calculated to be 1.000 µg/mL for the sterile preparation of purified corticotropin. This was calculated using a maximum dosing of 120 USP Units of the sterile preparation of purified corticotropin per day, which is greater than what is most commonly used in clinical application. The AET was also used as the reporting threshold for the study. The first study used extractions at 55±5° C. for 72±4 hours with agitation at approximately 100 RPM. The two extraction solvents evaluated were water, pH adjusted to 6.0±0.5 and 25% isopropanol. In the second study the extraction was performed on the inverted, fully assembled container closure system (CCS) (vial filled and stoppered with the rubber stopper) stored at 40±5° C. for 65±3 days (static). The drug product was used for the testing in the second study. No components were detected at or above the AET for this study.

An in-use stability study was performed over a period of 28 days in which the product was warmed, and a simulated dose was taken. This was repeated 5 times over this period and demonstrated that the CCS was integral after the 5 doses and justifies its use as a multi-dose product.

Example 2

Method development, qualification, and testing for activation of innate immune response was performed. The innate immune assays performed compared 3 PPQ lots. The work was conducted using 5 cell lines to cover TLR and NOD2 expression (THP-1 Blue, Raw Blue, HEK-blue hTLR3, HEK-Blue hTLR4, HEK-Blue hNOD2). Positive control ligands Poly (I:C) HMW, LPS-EK, FSL-1, CL075 and MDP were included in each assay. The results showed no dose responses at the concentrations tested, while the positive control ligands provided robust dose responses. The highest drug substance concentration tested was 10 µg/mL. A dose of the sterile preparation of purified corticotropin at 80 U is, equivalent to approximately 1 mg of drug substance per total body weight of subject. Thus, the results indicated little to no potential to elicit an innate immune response based on the concentrations tested.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within practice within the art to which the invention pertains and may be applied to the essential features herein before set forth.

The invention claimed is:

1. A kit comprising a vial and a sterile preparation of purified corticotropin, wherein the sterile preparation comprises 80 USP units per mL of corticotropin, phenol, type A gelatin, water for injection (WFI), hydrochloric acid, and sodium hydroxide, wherein the vial is not terminally sterilized, and
wherein the purified corticotropin comprises a polypeptide having an amino acid sequence of SYSMEHFRWGKPVGKKRRPVKVYPNGAEDELAEAFPLEF (SEQ ID NO: 1).

2. The kit of claim 1, further comprising instructions for using a first needle having a first gauge size with a first diameter to draw up the sterile preparation, and for injecting the sterile preparation using a second needle having a second gauge size with a second diameter.

3. The kit of claim 1, wherein the vial is a 5 mL multiple-dose vial.

4. The kit of claim 2, wherein the first diameter is wider than the second diameter.

5. The kit of claim 2, wherein the first gauge size is 20 G and the second gauge size is 23 G.

6. The kit of claim 1, wherein the sterile preparation comprises 0.5% w/w phenol, 15.0% w/w gelatin, and water for injection (WFI).

7. The kit of claim 1, wherein the sterile preparation comprises hydrochloric acid and sodium hydroxide.

8. The kit of claim 1, wherein the sterile preparation has a pH of 3.0-7.0.

9. The kit of claim 1, wherein the sterile preparation comprises purified corticotropin comprises an extract from whole porcine pituitary gland including both anterior and posterior portions of the whole porcine pituitary gland, 0.5% w/w phenol, 15% w/w gelatin type A, and water for injection (WFI).

10. The kit of claim 1, wherein the sterile preparation comprises about 15% w/w of the type A gelatin.

11. The kit of claim 1, wherein the sterile preparation comprises about 150 mg/ml of the type A gelatin.

12. The kit of claim 10, wherein the sterile preparation comprises about 0.1-1% w/w of the phenol.

13. The kit of claim 12, wherein the sterile preparation comprises about 0.5% w/w of the phenol.

14. The kit of claim 11, wherein sterile preparation comprises about 5 mg/ml of the phenol.

15. The kit of claim 1, wherein the kit further comprises instructions for use including washing hands and drying with a clean towel, removing the vial from a refrigerator, confirming that an expiration date on the vial has not passed, warming the gel in the vial from a solid gel to a liquid gel by rolling between hands for at least one minute, removing plastic cap from the top of the vial, wiping top of the vial stopper with a sterile alcohol wipe, using a sterile 20 G needle and syringe to draw up the warmed purified cortrophin gel from the vial, removing the 20 G needle, attaching a 23 G needle to the syringe, injecting the warmed purified cortrophin gel from the syringe into the subject.

16. The kit of claim 1, wherein the sterile preparation is preservative-free, antimicrobial-free, or preservative-free and antimicrobial-free.

17. The kit of claim 1, wherein the gelatin has a pH of 5.9 to 6.2.

18. The kit of claim 1, wherein the sterile preparation is free of acetic acid.

19. The kit of claim 1, wherein the gelatin is pyrogen-free.

20. The kit of claim 1, wherein the sterile preparation comprises acidified WFI having a pH of 2.8 to 3.2.

* * * * *

SEQUENCE LISTING

```
Sequence total quantity: 1
SEQ ID NO: 1              moltype = AA  length = 39
FEATURE                   Location/Qualifiers
source                    1..39
                          mol_type = protein
                          organism = unidentified
SEQUENCE: 1
SYSMEHFRWG KPVGKKRRPV KVYPNGAEDE LAEAFPLEF                                39
```